United States Patent [19]

Liu

[11] Patent Number: 4,755,504

[45] Date of Patent: Jul. 5, 1988

[54] PHARMACEUTICAL COMPOSITION FROM TIENCHI

[76] Inventor: Yaguang Liu, 67-08 168th Street, Fresh Meadows, N.Y. 11365

[21] Appl. No.: 944,357

[22] Filed: Dec. 22, 1986

Related U.S. Application Data

[63] Continuation-in-part of Ser. No. 783,665, Oct. 3, 1985, abandoned.

[51] Int. Cl.$^4$ ............................................. A61K 35/78
[52] U.S. Cl. .......................................... 514/26; 536/5; 536/6.3; 536/8; 426/658; 514/822; 514/825
[58] Field of Search .......................... 514/26, 822, 825; 426/658; 536/5, 6.3, 8

[56] References Cited

U.S. PATENT DOCUMENTS

| | | | |
|---|---|---|---|
| 3,661,890 | 5/1972 | Jurd | 536/8 |
| 3,929,996 | 12/1975 | Higuchi | 514/26 |
| 4,157,894 | 6/1979 | Bombardelli | 536/5 |
| 4,171,430 | 10/1979 | Matsushita et al. | 536/8 |
| 4,339,442 | 7/1982 | Takemoto et al. | 514/26 |
| 4,621,076 | 11/1986 | Kuzuya et al. | 514/822 |

FOREIGN PATENT DOCUMENTS 2056855  3/1981  United Kingdom ................. 514/26

*Primary Examiner*—Ronald W. Griffin
*Attorney, Agent, or Firm*—Chenpatents

[57] ABSTRACT

A pharmaceutical composition containing saponin and quercetin, derived from Tienchi, is effective in treatment of circulatory disease and as health food. Processes for producing these components are provided.

16 Claims, No Drawings

PHARMACEUTICAL COMPOSITION FROM TIENCHI

This application is a continuation-in-part of my earlier co-pending application, Ser. No. 783,665 filed on Oct. 3, 1985 to be abandoned as of the filing date of this application.

BACKGROUND OF THE INVENTION

1. Field of the Invention

This invention relates to a new pharmaceutical composition comprising two active ingredients: quercetin and saponin derived from the root Tienchi, the Chinese name of Panax Notoginseng (Burk) F. H. Chen, a member of the ginseng family growing in the provinces of Yunnan and Guangxi in Southern China. Tienchi is the source of a valuable Chinese traditional medicine for human consumption.

2. Description of Prior Art

In recent years, there has been much interest in plant-derived health foods and medicines, particularly ginseng. There are many varieties of ginseng and each variety of the ginseng plant contains many pharmacologically active components. Correctly chosen mixtures of such components often have unexpected benefical effects. The prior art usually addresses the preparation of such components alone in pure form.

U.S. Pat. No. 3,661,890 discloses a process for converting rutin into 3-O-alkyl quercetin by organic synthesis. Two alkyl quercetin derivatives are reported to have antimicrobial activity.

U.S. Pat. No. 4,339,442 discloses a group of saponins which have been isolated from Gynostemma pentaphyllum Makino of Cucurbitacease and pharmacutical use thereof.

Thus far, there has been no disclosure of a composition containing quercetin and saponin derived from Tienchi and its pharmacological activity in the treatment of circulatory disease.

SUMMARY OF THE INVENTION

One objective of this invention is to provide a pharmaceutical composition comprising quercetin and saponin for treatment of circulatory disease and as a health food. The other objective is to provide an economical and efficient process for preparing such a composition by extracing the root of Tienchi, which contains quercetin and saponin, and passing the extract through two resin columns in sequence, thereby adsorbing both quercetin and saponin in the first column, then selectively eluting saponin and adsorbing saponin in the second column and then eluting the same; and eluting quercetin from the first column; purifying crude saponin and quercetin separately; and then preparing a mixture of the pure components having 80–95.5 wt.% of saponin; and 0.5–20 wt. % of quercetin.

DETAILED DESCRIPTION OF THE INVENTION

The pharmaceutical composition of this invention comprises quercetin and saponin derived from the root of Tienchi.

The structural formula of quercetin, (I), is as follows:

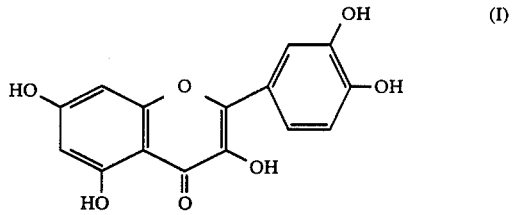

Melting point of quercetin is 313°–315° C.

The general structural formula of two forms of saponin is as follows:

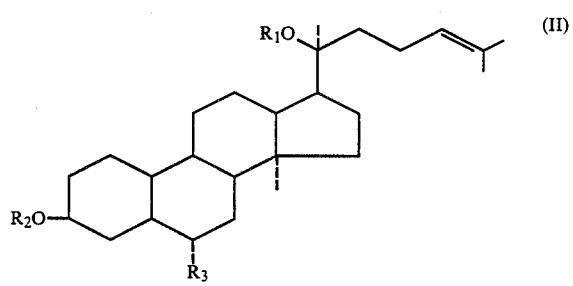

Where
$R_1$ is glucose 6   1 glucose
$R_2$ is glucose 2   1 glucose
$R_3$ is H
the compound is saponin $Rb_1$;
Where
$R_1$ is glucose
$R_2$ is H
$R_3$ is glucose
the compound is saponin $Rg_1$.

The structural formula of saponin $Rb_1$, (III) is as follows:

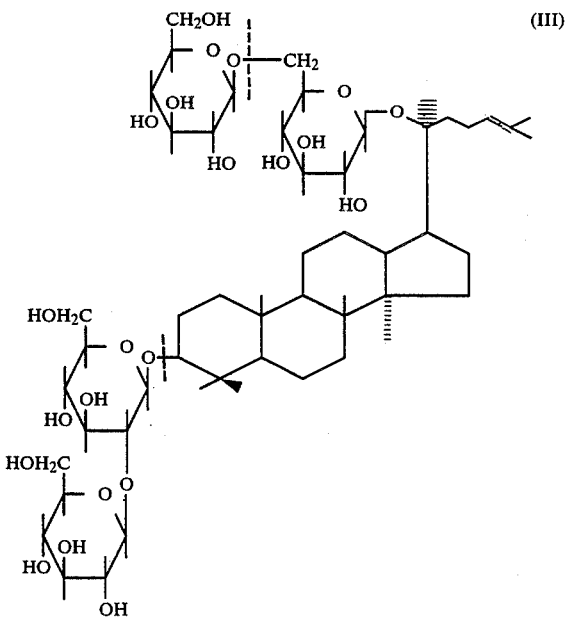

SAPONIN Rb-1

The structural formula of saponin $Rg_1$, (IV) is as follows:

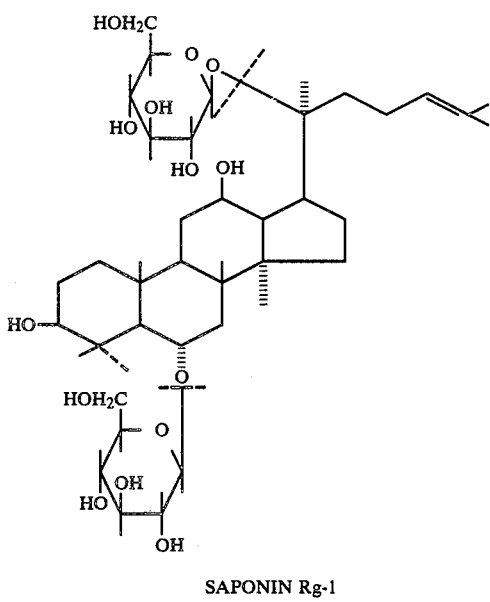

SAPONIN Rg-1

The mixture of saponin Rb$_1$ and saponin Rg$_1$ has a melting point range of 189°–209° C.

The invention is first described with respect to the production of the pharmaceutical composition and health foods. The process comprises the extraction of a mixture of quercetin and saponin from the root of Tienchi with ethanol, preferable 80% ethanol; concentration of the extract by vacuum distillation; isolation of pure saponin and quercetin by a two-stage process of column chromotography with different resin packings; purification of the crude components and mixing the pure components to yield a composition of 80–95.5 weight saponin and 0.5–20 weight percent of quercetin. A more detailed process of isolating quercetin and saponin is illustrated by the following examples.

EXAMPLE 1

One kilogram of dried powder of Tienchi roots was extracted with 10 liters of 80% ethanol for 24 hours. The extraction was repeated two more times in the same manner. The three ethanol extracts were combined and reduced to 1 liter by vacuum distillation. The resulting concentrated ethanol extract was passed through a column packed with polyamide resin, 5.3 cm in diameter and 50 cm long. Saponin and quercetin were absorbed by the resin packing. The saponin was then selectively eluted by passage of distilled water through the column at a rate of 10 ml/min. The aqueous saponin elate was saved for later recovery of saponin as described below. The quercetin still adsorbed on the resin packing was then eluted with 10%, 20% and 30% ethanol in sequence at a rate of 10 ml/min. The three ethanol eluates were combined and concentrated by vacuum distillation. Yellow needle-like crystals of crude quercetin were thus obtained. These crystals were dissolved in an ethanol-water mixture and recrystallize to produce pure quercetin.

The aqueous saponin solution was passed through a polybenzene-ethylene (Dowex 50) macroreticular resin column to adsorb both forms of saponin, namely saponin Rb$_1$ and Rg$_1$ selectively. The adsorbed saponin was then eluted from the resin column with 60% and 70% ethanol in sequence. The ethanol eluates were combined and concentrated by vacuum distillation.

Two volumes of acetone per volume of concentrated ethanol eluate were then added with agitation, and a yellow-white powder was precipitated. This powder was separated by filtration, and the filtrate was reduced to 100 ml by vacuum distillation. This concentrated filtrate was added to 1000 ml of fresh acetone, and a yellow-white precipitate was again obtained. The second precipitate was separated by filtration, and the filtercakes from both filtrations were combined. They were washed twice with acetone and twice with diethyl ether, and dried. The product thus obtained was pure saponin.

EXAMPLE 2

Alternatively, quercetin and saponin may be prepared in the following manner.

1 Kg. of dried powder of Tienchi roots was extracted with 10 liters of 95% ethanol for 24 hours. The extraction was repeated two more times in the same manner. The extracts were combined and concentrated to 1 liter as described in Example 1. The concentrated ethanol solution was extracted five times each with 1 liter of n-butanol to yield a n-butanol layer (A) and an ethanol layer (B). The two layers were separated by decantation into (A) layer containing saponin and (B) layer containing quercetin.

Recovery of Saponin

The n-butanol layers (A) were distilled under vacuum to recover n-butanol and a residue. The residue was dissolved in 300 ml ethanol and filtered to remove impurities. The filtrate was mixed with 2 liters of acetone with stirring. A yellow-white powder was precipitated and recovered by filtration. The acetone filtrate was concentrated to 100 ml and then added to 1 liter of fresh acetone to recover a second precipitate. The two precipitates of crude saponin were washed twice with acetone and twice with diethyl ether and dried to produce pure saponin.

Recovery of Quercetin

The ethanol layers (B) were passed through a sephadexLH20 column (5.2 cm. in diameter×59 cm in length). The adsorbed quercetin was eluted with distilled water at a rate of 10 ml/min and then further eluted with 0.1M ammonium hydroxide. An equal volume of ethyl acetate was added to the ammonium hydroxide eluate with stirring. The elution with dilute ammonium hydoxide and the addition of ethyl acetate processes were repeated three times. The resulting ethyl acetate solution was distilled under vacuum. Crude quercetin in the form of yellow needle-like crystals was obtained. Crude quercetin was recrystallized from an ethanol-water mixture, separated therefrom by filtration, and washed twice with diethyl ether and twice with chloroform and dried. The product is pure quercetin.

Production of Sodium Quercetin

In another embodiment, a sodium salt of quercetin was produced by suspending 100 mg. quercetin in 800 ml distilled water, acidified to pH 2 with a mineral acid. To this solution was added aqueous sodium carbonate to bring the pH to 7. This neutral solution was filtered and the filtrate was concentrated to a syrupy consistency by vacuum distillation. The syrup was then vacuum dried to form a powder sodium quercetin.

The composition used as a drug or health food, comprises 80–95.5 weight percent of saponin and 0.5–20 weight percent of quercetin or its sodium salt, the preferred composition being 90% by weight of saponin and 2% by weight of quercetin or its sodium salt. This composition is comsumed as tea or taken in the form of capsules, tablets or syrup, after being incorporated in a carrier such as sugar, starch, or other materials known in the art.

Each capsule or tablet contains about 50–250 mg. of the composition which is equivalent to 0.6–3.0 g. of dried Tienchi root. Each tea bag contains 20–100 mg. of the composition, with or without the addition of tea or herbs to suit individual tastes.

The composition is now described with respect to its pharmacological effects in vivo or in vitro. The composition is referred to as ACT in the following examples.

EXAMPLE 4

The Effect of ACT on the Survival Rate of Myocardial Cells under Hypoxia

A culture of chick heart cells was prepared by standard method: Chicken hearts were removed from embryos and were dissociated at 37° C. for 45 minutes with 0.25% trypsin (sigma, type III), 0.025% collagenase (sigma, type I), and 0.005% pancreatin ($NBC_0$), prepared in calcium and magnesium-free saline G containing 4% chicken serum. The heart tissue was dispersed into a single cell suspension in culture medium containing 5 mg/ml DNAse I (sigma). Viable cell counts were determined by hemocytometer counting. Cells were dispersed into 60 mm culture dishes, each having a surface area of 2000 $mm^2$ and the contents thereof having a density of 200 cells/$mm^2$.

Cultures were maintained in Ham's F-12K cln, a medium for myocardial cells, supplemented with 5% fetal bovine serum and gentamicin (5 mg/100 ml). Tissure culture dishes were incubated under 5% $CO_2$ and 95% air at 37° C.

All cells were counted in 20 randomly selected fields across the entire dish. A Zeiss microscope 25× objective having a field of view of 0.32 $mm^2$ was used for cell counting.

Chick myocardial cells were divided into three groups after having been added to the culture and left under normal condition for one day. The three groups are normal, control and ACT. The conditions which the three groups are subjected to are listed in Table 1.

TABLE 1

| | Experimental Conditions | |
|---|---|---|
| | culture in experiment | |
| group | gas | medium |
| normal | 5% $CO_2$ + 95% air | normal |
| control | 5% $CO_2$ + 95% $N_2$ | sugar deficiency |
| ACT | 5% $CO_2$ + 95% $N_2$ | sugar deficiency + 50 ACT/ml |

The sugar deficient media were left in the incubator, under 5% $CO_2$ and 95% air, for 15 minutes to expell any existing oxgen. All three groups were incubated for 6 hours under their respective conditions.

Preparation of autoradiograms

Cells were labelled for two hours with a medium containing 5 $\mu$Ci/ml methyl-$^3$H-thymidine (New England Nuclear) at a specific activity of 50.8 Ci/mole. After labelling, dishes containing labelled cells were rinsed with saline, fixed in 1:9 formalin-ethanol, stained with periodic acid-schiff (PAS) and coated with Kodak NTB-3 emulsion, a nuclear emulsion diluted 1:1 with water.

Autoradiograms were exposed for seven days, then developed in Dektol, counterstained with 1% aqueous fast green and air dried.

At least 1000 nuclei per culture were counted at random and cells having more than 50 silver grains over the nucleus were scored as positive labelling. The background was usually less than 5 grains. The cellular density of each culture was also determined by recording the number of microscopic fields counted to assess the total area scored. The results of the experiments are shown in Table 2.

TABLE 2

| The Effect of ACT on Myocardial Cells Under Hypoxia | | |
|---|---|---|
| Percent of myocardial cell nuclei labelled | | |
| normal | control | ACT |
| 19.0 ± 1.2 (*3) | 9.6 ± 0.51 (*10) | 13.1 ± 0.60 (*10) |
| — | $P < 0.01$ | |

From the above Table 2, it is apparent that ACT increases the myocardial cells survival rate as measured by labelled cell nuclei, from 9.6 without ACT to 13.1 with ACT under the same conditions of hypoxia. This means that ACT increases DNA synthesis of myocardial cells under hypoxia by 36%.

EXAMPLE 5

The Effects of ACT on Cardiovascular Functions

Case 1, The Effect of ACT on Coronary Blood Flow

A known method for testing the effect of ACT on coronary flood flow was followed. Perfused isolated hearts of guinea pigs were used. The experimental results are shown in Table 3 below, which demonstrates that ACT increases the coronary blood flow by 72.7% from that of the control.

TABLE 3

| The Effect of ACT on Coronary Blood Flow | |
|---|---|
| mean coronary blood flow | |
| before ACT | after ACT (35 mg/ml) |
| 9.9 ± 0.9 (*10) | 17.1 ± 0.18 (*10) |
| | $P < 0.001$ |

Case 2, The Effect of ACT on the Oxygen Consumption of Myocardial Hemogenate

This experiment was performed according to Warburg's monometry method (Richard A. D.: J. Am. Pharm. Asso. 45: 562, 1956) Pyruvate was used as substrate. The results of the experiment are summarized in Table 4, which show that with ACT, the oxygen consumption of the heart muscle per hour is 99 $\mu$l/100 mg in comparison with 218.3 $\mu$l/100 mg of the control (without ACT).

TABLE 4

| The Effect of ACT on the Oxygen Consumption of myocardial hemogenate | |
|---|---|
| | oxygen consumption $\mu$l/100 mg heart muscle/hour |
| control group | 218.3 ± 9.9 (*20) |
| ACT group | 99.0 ± 5.4 (*20) |

TABLE 4-continued

The Effect of ACT on the Oxygen Consumption
of myocardial hemogenate

| | oxygen consumption<br>μl/100 mg heart muscle/hour |
|---|---|
| P | <0.01 |

EXAMPLE 6

The Effect of ACT on Aggregation of Platelets

A blood sample was secured by cardiac pucture of rabbit heart with a silicon-coated syringe. The blood was mixed with 3.8% sodium citrate in the ratio of 9:1 to prevent clotting. The blood sample was centrifuged at 1000 rpm for 6 minutes. 1 ml of the platelet-rich plasma was aspirated and transferred to a silicon-coated 2 ml cell. The blood sample was well stirred and transmittance (Ti) was read with a spectrophotometer. 0.02 ml of ADP at a concentration of 2 μM/ml was added to the blood sample, which is stirred constantly and transmittance of the platelet plasma was read once every minute. The maximum transmittance (Tm) was read within ten minutes.

Another portion of the blood sample was centrifuged at 3000 rpm for 45 minutes and the transmittance of a platelet-poor plasma was read (To). The platelet aggregation rate was calculated by the following formula:

$$\frac{Tm - Ti}{To - Ti} \times 100$$

Results of the experiment on the aggregation rate of platelets are shown in Table 5, which shows that with ACT, the aggregation rate of platelets is 21.6% comparing with 54.1% of the control. This is interpreted that ACT decreases the aggregation of platelets by 60%.

TABLE 5

Aggregation Rate of Platelets
aggregration rate of platelet (%)

| control group<br>(normal saline) | ACT group<br>(1 mg/ml plasma) |
|---|---|
| 54.10 ± 8.9 (*12) | 21.6 ± 1.89 (*12) |
| P < 0.001 | |

EXAMPLE 7

The Effect of ACT on Analgesic Reaction in Vitro

This experiment is to measure the resistance to burn in rats by measuring the "threshold pain" following the "hot plate" method. The experimental results are shown in Table 6 which shows that the "threshold pain" for the rat was raised by intrapertoneal injection of ACT at a dose of 150 mg./Kg. from 19.1 for the control to 36.9.

TABLE 6

Effect of ACT on Analgesic Reaction of Rats

| group | threshold pain | |
|---|---|---|
| | basic | after injection 30 min. |
| control | 18.9 ± 0.9 | 19.1 ± 0.6 (*20) |
| ACT | 18.9 ± 0.9 | 36.9 ± 0.9 (*20) |
| P | | <0.001 |

EXAMPLE 8

The Effect of ACT on Antiinflammation in Mice

Mice were injected hyodermically with 20 ml. of air at the back of each mouse to cause gas vesicle. 0.5 ml of croton oil was then injected into the gas vesicle to induce an inflammation. Every day, the mice in the control group were intraperitoneally injected with normal saline, and the mice in the ACT group, with ACT at a dose of 250 mg/Kg. After six days, the mice were killed. The volume of exudation of each mouse was determined. Results of the experiment are shown in Table 7, which indicates ACT significantly inhibits the increase of capillary permeabilities (exudation) induced by croton oil. Thus the antiinflammatory activity is increased threefold by ACT from that of the control

TABLE 7

| | Exudation Volume<br>exudation |
|---|---|
| normal | 6.09 ± 0.36 (*10) |
| ACT | 2.41 ± 0.23 (*10) |
| P | <0.01 |

The toxicity of ACT has been found very low, thus ACT is safe. The $LD_{50}$ of ACT was determined to be 1041 mg/Kg followed by injection of ACT in the abdominal cavity of mice.

The above experiments demonstrate that treatment with ACT improves all the important functions of the circulatory system, such as coronary blood flow, oxygen consumption of the heart muscle, aggregation of platelets etc.

It is to be understood that the embodiments and examples described herein can be modified and such modifications are within the spirit and scope of the present invention, as is defined by the appended claims.

I claim:

1. A composition pharmaceutically suitable for treatment of circulatory disease comprising: saponin 80-95.5 wt. %; and quercetin 0.5-20 wt. %.

2. A composition of claim 1 wherein saponin is in the form of saponin $Rb_1$ and saponin $Rg_1$.

3. A composition of claim 1 wherein saponin and quercetin are derived from root extract of Panax Notoginseng (Burk) F. H. Chen.

4. A method of treating circulatory disease in a human suffering therefrom comprising: administering to said human an effective dose of a composition of claim 1.

5. A method of treating circulatory disease in a human suffering therefrom comprising administering to said human an effective dose of a compositin of claim 2.

6. A method of treating circulatory disease in a human suffering therefrom comprising administering to said human an effective dose of a composition of claim 3.

7. A health food in the form of tea, tablets or capsules, each comprising a net weight of 50-250 mg. of a composition of claim 3.

8. A composition pharmaceutically suitable for treatment of inflamation comprising 80-95.5 wt. % of saponins and 0.5-20 wt.% of quecertin.

9. A composition pharmaceutically suitable for lowering aggregation of platelets activity comprising 50-250 mg per dose of a composition of claim 1.

10. A process for producing a pharmaceutical composition of claim 3 comprising:

a. extracting powder root with ethanol and recovering extract;
b. concentrating the extract by vacuum distillation;
c. passing the concentrated extract of (b) through a polyamide resin column;
d. passing distilled water through said column to elute adsorbed saponin, and recovering the same;
e. passing 10–30% of ethanol through the column to elute adsorbed quercetin;
f. concentrating ethanol eluate from (e) by vacuum distillation to crystallize quercetin;
g. passing aqueous saponins of (d) through a polybenzeneethylene macrorecticular resin column to adsorb saponin;
h. eluting the adsorbed saponin with 60–70% ethanol;
i. concentrating ethanol eluate by vacuum distillation;
j. precipitating saponin by mixing the concentrated eluate of (i), with acetone and recovering saponin from acetone; and
k. washing the crude saponin with acetone and diethyl ether respectively, followed by drying; and
l. mixing pure saponin and quercetin.

11. A process of claim 10 further comprising the step of concentrating acetone of (j) and mixing therewith fresh acetone thereby residual saponin is recovered.

12. A process of claim 11 further comprising the step of recrystallizing quercetin of (f) from ethanol-water.

13. A process for producing sodium salt of quercetin comprising:
   a. suspending solid quercetin in acidic distilled water;
   b. slowly adding sodium carbonate till the solution is neutral;
   c. filtrering and concentrating the filtrate to syrup under vacuum to yield a dry sodium quercetin powder.

14. A composition of claim 1 wherein quercetin ia a sodium salt of quercetin.

15. A health food of claim 7 wherein quercetin is a sodium salt of quercetin.

16. A method of treating circulatory disease in a human suffering therefrom comprising admininstering to said human an effective dose of a composition of claim 14.

* * * * *